United States Patent
Pettigrew et al.

(10) Patent No.: US 7,271,306 B2
(45) Date of Patent: Sep. 18, 2007

(54) HEAT RECOVERY FROM THE EFFLUENT STREAM OF AN OXYGENATE-TO-OLEFIN PROCESS

(75) Inventors: Malcolm G. Pettigrew, Houston, TX (US); Wadie Malaty, Houston, TX (US); Ram Mohan Lai Mallik, Houston, TX (US); Stephen W. McCormick, Spring, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 700 days.

(21) Appl. No.: 10/763,024

(22) Filed: Jan. 22, 2004

(65) Prior Publication Data
US 2004/0152936 A1 Aug. 5, 2004

Related U.S. Application Data

(60) Provisional application No. 60/442,358, filed on Jan. 24, 2003.

(51) Int. Cl.
*C07C 1/00* (2006.01)
(52) U.S. Cl. .................................... 585/640; 585/910
(58) Field of Classification Search ................ 585/640, 585/910
See application file for complete search history.

(56) References Cited

U.S. PATENT DOCUMENTS

| | | |
|---|---|---|
| 4,929,780 A | 5/1990 | Wright et al. |
| 5,028,400 A | 7/1991 | Harandi et al. |
| 6,121,504 A | 9/2000 | Kuechler et al. |
| 6,403,584 B1 | 6/2002 | de Laszlo et al. |

*Primary Examiner*—Glenn Caldarola
*Assistant Examiner*—In Suk Bullock

(57) ABSTRACT

The present invention comprises a process for cooling a reactor effluent stream from a methanol-to-olefins reactor. The process is efficient and recovers heat from the reactor effluent stream in one or more highly usable forms, preferably high pressure superheated steam.

14 Claims, 1 Drawing Sheet

HEAT RECOVERY FROM THE EFFLUENT STREAM OF AN OXYGENATE-TO-OLEFIN PROCESS

CROSS REFERENCE TO RELATED APPLICATIONS

The present application claims the benefit of U.S. Provisional Application No. 60/442,358, filed Jan. 24, 2003, said application is incorporated herein by reference.

FIELD OF THE INVENTION

The present invention relates to a process for recovering heat from an oxygenate-to-olefin effluent stream.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefin(s). The preferred oxygenate for light olefin production is methanol. The process of converting methanol-to-olefins is called the methanol-to-olefin(s) process. There are numerous technologies available for producing oxygenates, and particularly methanol, including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming or a combination thereof.

Syngas is then processed into methanol. Specifically, the components of syngas (i.e., hydrogen, carbon monoxide and/or carbon dioxide) are catalytically reacted in a methanol reactor in the presence of a heterogeneous catalyst. For example, in one synthesis process methanol is produced using a copper/zinc oxide catalyst in a water-cooled tubular methanol reactor.

The methanol-to-olefins reaction is highly exothermic. Moreover, this reaction has a large amount of water. Water comprises as much as one half of the total weight of the effluent stream to isolate the olefins the effluent stream. Consequently, the water must be removed by condensation in a quench device to isolate the olefin product. The quench device cools the effluent stream to the condensation temperature of water. Quenching the product recovers large quantity of water at the temperature near the boiling point of the quench water. It is desirable to recover heat in higher temperature streams before quenching. Thus, it is one object to recover as much of the heat of the effluent stream before the effluent stream is quenched.

U.S. Pat. No. 6,403,854 is a process of converting oxygenates to olefins with direct product quenching for heat recovery. U.S. Pat. No. 6,403,854 teaches using the reactor effluent stream to cool the effluent stream and superheat the methanol feed stream. Thereafter, the effluent stream is passed to a first stage quench tower of a two-stage quench system.

U.S. Pat. No. 6,121,504 illustrates a process for converting oxygenates to olefins with direct product quenching for heat recovery. According to this patent, the effluent stream may be used to provide heat directly to an oxygenate feedstock. Disclosed is a single heat transfer device for accomplishing this heat exchange between the effluent stream and the oxygenate feedstock.

Nonetheless, there is still a need to recover more heat from the reactor effluent stream in a more efficient manner. The present invention satisfies these and other needs.

SUMMARY OF THE INVENTION

The present invention comprises a process for cooling a reactor effluent stream from a methanol-to-olefins reactor. The process is efficient and recovers heat from the reactor effluent stream in one or more highly usable forms. According to one embodiment, the process comprises several of the following steps. First, a methanol feed stream is supplied to the reactor in a methanol-to-olefins conversion process. In the reactor, the methanol feed stream is contacted with a molecular sieve catalyst composition. One or more olefin products are produced. High pressure saturated steam, in one embodiment, is heated with the reactor effluent stream to produce high pressure superheated steam, typically in a first heat exchanger. This heating of the high pressure saturated steam results in a first cooled effluent stream.

In another embodiment, a first water stream is heated with the first cooled effluent stream, typically in a second heat exchanger. High pressure saturated steam and a second cooled effluent stream are produced. In one embodiment, the high pressure saturated steam from the first heat exchanger is supplied to the second heat exchanger. Alternatively, a second water stream is heated with the second cooled effluent stream, typically in a third heat exchanger. The heating of the second water stream results in a third cooled effluent stream. Additionally and optionally, a methanol feed stream is heated with the third cooled effluent stream, typically in a fourth heat exchanger. The heating of the methanol feed stream results in a fourth cooled effluent stream.

In another embodiment, there is a process for producing one or more olefin products from a methanol feed stream in a reactor. According to one embodiment of the process methanol feed stream is supplied to the reactor. The methanol feed stream is contacted with a molecular sieve catalyst composition in the reactor to produce an effluent stream. In step (a), high pressure steam is heated with the effluent stream. In step (b) following step (a), medium pressure steam is heated with the effluent stream. Then, one or more olefin products are recovered from the effluent stream. In one embodiment, step (a) has a first sub-step. In the first sub-step of step (a), high pressure saturated steam is heated with the effluent stream to produce high pressure superheated steam. Following the first sub-step, a second sub-step occurs. In the second sub-step, water is heated with the effluent stream to produce the high pressure saturated steam. Alternatively, there is an additional step (c) following step (b) where the methanol feed stream is heated with the effluent stream.

In yet another embodiment, there is a process for heating methanol in a methanol feed stream. The process comprises the steps of: (a) heating with a heat source a methanol feed stream; (b) supplying the methanol feed stream to a reactor; (c) contacting the methanol feed stream with a molecular sieve catalyst composition in the reactor and removing a reactor effluent stream; and (d) cooling the reactor effluent stream in no less than three heat exchangers to produce a cooled effluent stream. According to this process, the cooled effluent stream is the heat source for the step (a) heating.

In still another embodiment, there is a process for producing one or more olefin products from methanol in a reactor. The process comprises the steps of: (a) supplying a methanol feed stream to the reactor; (b) contacting the methanol feed stream with a molecular sieve catalyst composition in the reactor and withdrawing a reactor effluent stream having a first temperature; (c) cooling the reactor effluent stream in no less than four stages to produce a cooled effluent stream. Each of the four stages decreases the temperature by no less than 50° F. (10° C.). The cooled effluent stream has a second temperature that is at least 500° F. (260° C.) less than the first temperature.

DETAILED DESCRIPTION OF THE INVENTION

Introduction

Figure 1:
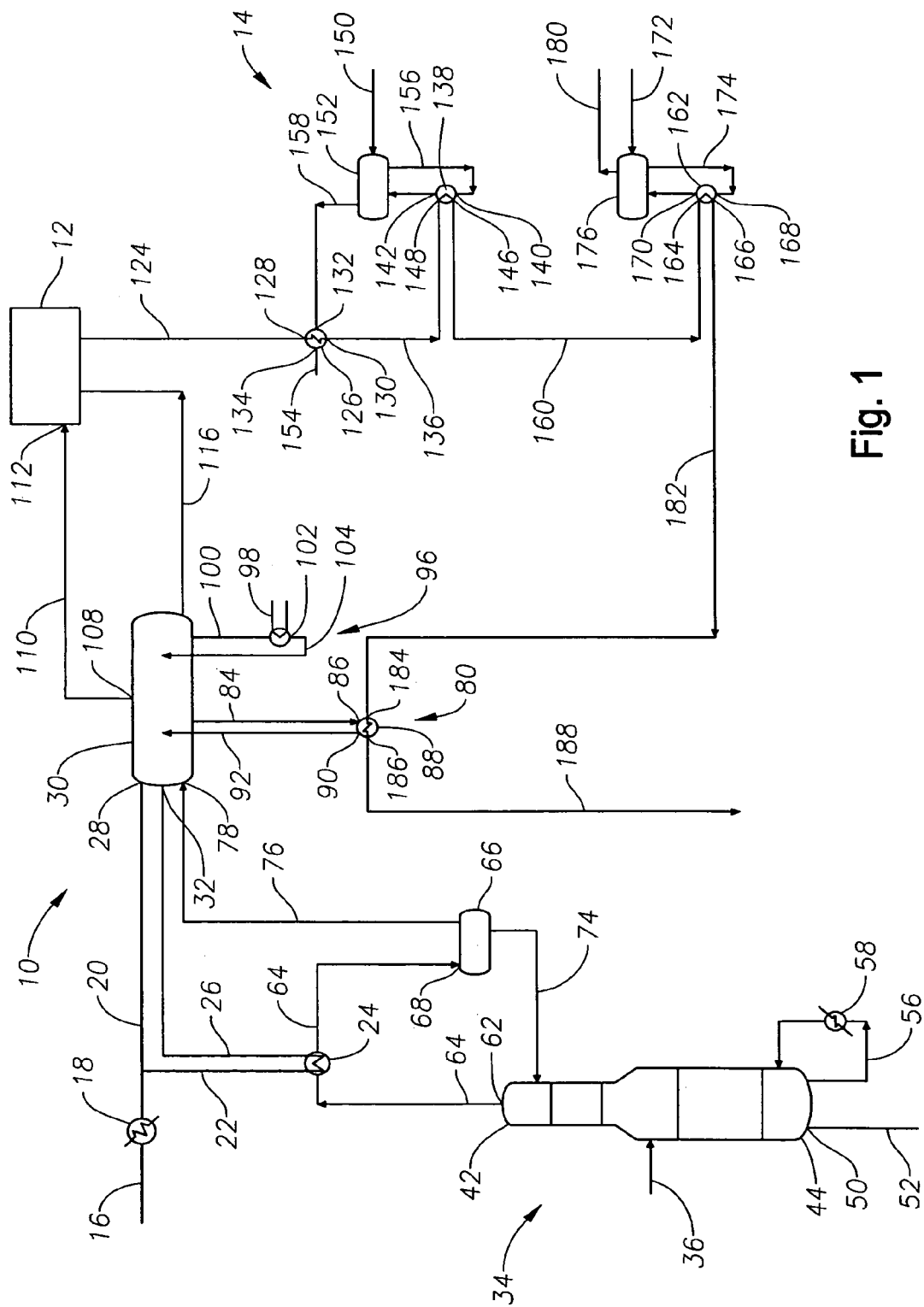
FIG. 1 illustrates a process scheme according to one embodiment of the present invention.

The present invention comprises a process for cooling a reactor effluent stream from a methanol-to-olefins reactor. The process is efficient and recovers reactor effluent stream in one or more highly usable forms of heat, preferably high pressure superheated steam.

By way of example, the present invention of one embodiment is a process for producing one or more olefin products from methanol in a reactor. The process comprises the steps of: (a) supplying a methanol feed stream to the reactor; (b) contacting the methanol feed stream with a molecular sieve catalyst composition in the reactor and withdrawing a reactor effluent stream having a first temperature; (c) cooling the reactor effluent stream in no less than four stages to produce a cooled effluent stream. According to one embodiment, each of the four stages decreases the temperature by no less than 50° F. (10° C.), preferably no less than 75° F. (42° C.), more preferably no less than 100° F. (56° C.), even more preferably no less than 125° F. (69° C.), and most preferably non less than 150° F. (83° C.). In another embodiment, the cooled effluent stream has a second temperature that is at least 500° F. (260° C.), preferably at least 600° F. (333° C.); more preferably at least 700° F. (389° C.), even more preferably at least 800° F. (444° C.), and most preferably at least 900° F. (500° C.) less than the first temperature.

The process of one or more embodiments including, (1) the oxygenate to olefin reaction, (2) cooling the reactor effluent stream and recovering heat, (3) quenching the cooled effluent stream, and (4) recovering and using olefin products are described below.

The Oxygenate-To-Olefin Process

The molecular sieve catalyst compositions are particularly useful in processes for conversion of a feedstock containing one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols that are useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, and most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock and most preferably a methanol containing feedstock, is converted in the presence of a methanol-to-olefins catalyst or catalyst composition. In one embodiment, the catalyst or catalyst composition is molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent.

As noted, oxygenate-to-olefin processes use molecular sieve catalysts or catalyst compositions. The molecular sieve catalysts or catalyst compositions have molecular sieve and binder and/or matrix material. The molecular sieve catalysts are prepared according to techniques that are known to a person of ordinary skill in the art.

Molecular sieve include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, AFO, AEL, EUO, HEU, FER, MEL, MFI, MTW, MTT, TON, EMT, FAU, ANA, BEA, CFI, CLO, DON, GIS, LTL, MER, MOR, MWW and SOD and substituted forms thereof; and the large pore molecular sieves. Preferably the molecular sieve is a zeolitic or zeolitic-type molecular sieve. Alternatively, the preferred molecular sieve is an aluminophosphate (ALPO) molecular sieves and silicoaluminophosphate (SAPO) molecular sieves and substituted, preferably metal substituted, ALPO and SAPO molecular sieves including the molecular sieves that are intergrowth materials having two or more distinct phases of crystalline structures within one molecular sieve composition.

Binder materials that are useful alone or in combination include various types of hydrated alumina, silicas, and/or other inorganic oxide sol. In one embodiment, the binders are alumina sols including include Nalco 8676 available from Nalco Chemical Co., Naperville, Ill., and Nyacol available from The PQ Corporation, Valley Forge, Pa.

Matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, and most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite, zeolite-type molecular sieve catalyst, silicaluminophosphate catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 1 weight percent to about 10 weight percent based on the total weight of the feedstock including any diluent contained therein. The liquid and vapor feedstocks are preferably of similar composition, or contain varying proportions of the same or different feedstock with the same or different diluent.

The feedstock entering the reactor system is preferably converted, partially or fully, in the first reactor zone into a effluent stream that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the effluent stream containing one or more olefin(s) within the disengaging zone. Cyclones are preferred, however, gravity effects within the disengaging vessel will also separate the catalyst compositions from the effluent stream. Other methods for separating the catalyst compositions from the effluent stream include the use of plates, caps, elbows, and the like. Cyclones are particle size separators and retain catalyst above a threshold size. Catalyst below a threshold size pass through the cyclones in the effluent stream. As defined above, catalyst particles are retained by the cyclones in the reactor. Catalyst fines pass through the cyclones into the effluent stream.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from about 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C., and most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically, the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock-containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate-to-olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See, for example, U.S. Pat. No. 5,952,538 that is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kpaa) to about 250 psia (1724 kpaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the effluent stream (PCT WO 00/49106 published Aug. 24, 2000), which are all herein fully incorporated by reference. In another embodiment, a regenerated molecular sieve catalyst composition contacted with an alcohol, preferably ethanol, 1-propanol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336-337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator. This is referred to as the partial regeneration mode.

Coke levels, or the level of carbonaceous deposits, on the molecular sieve catalyst composition are measured by withdrawing from the conversion process the molecular sieve catalyst composition at a point in the process and determining its carbon content.

In one preferred embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. A person of ordinary experience would recognize that the molecular sieve catalyst composition in the reaction zone is made up of a mixture of regenerated catalyst and catalyst that has ranging levels of carbonaceous deposits. The measured level of carbonaceous deposits thus represents an average of the levels an individual catalyst particle.

Methanol Feed Vaporization System and Heat Recovery from the Effluent Stream

The present invention pertains in general terms to efficiently recovering heat from an oxygenate-to-olefin reactor system. The oxygenate-to-olefin reactor system is the complete system of taking an oxygenate feedstock, typically methanol, and converting it to one or more olefin products and then recovering the one or more products. The oxygenate to olefin reactor system comprises, without limitation, the methanol feed vaporization system 10, the reactor 12, the effluent heat recovery system 14, and a product recovery system (not illustrated).

One, non-limiting embodiment of the present invention is illustrated in FIG. 1. A methanol feed stream comprising methanol is transported along line 16 to a feed stream heat exchanger 18. The methanol feed stream continues along line 20 and into the methanol feed vaporization drum 30 through inlet 28. The methanol feed stream is primarily supplied through line 16.

Alternatively or additionally, a second source of methanol for the oxygenate-to-olefins reactor is unreacted methanol feed. The unreacted methanol feed is recovered, in one embodiment, from the effluent stream that produced the oxygenate-to-olefin reactor 12. The effluent stream is typically quenched in a quench device (not shown) to condense water and form a liquid stream in the bottom of the quench device called a quench bottoms stream. The unreacted methanol feed is present in quench bottoms stream. Additionally, other locations in the process where water is condensed often contain unreacted methanol feed that can be recovered and sent to the reactor by combining it with the quench bottoms stream. The quench bottoms stream is fed along an aqueous feed line 36. The quench bottom stream passes into a fractionation tower 34.

One example of how water is recovered is provided without limitation below. The fractionation tower 34 performs a step of separating unreacted methanol feed from water. The fractionation tower 34, of one embodiment, has a top end 42 and a bottom end 44. A stream of primarily unreacted methanol feed is withdrawn through outlet 62 in the top end 42 and is referred to herein as the overhead stream. Overhead stream passes along line 64 into overhead flash drum 66. As the overhead stream passes along line 64, it is cooled in overhead condenser 24 by a portion of the methanol feed stream.

Particularly, line 22 transports a portion of the methanol feed stream to the overhead condenser 24. The overhead stream is cooled and at least partially condensed. The methanol feed stream is heated. The methanol feed stream that passes through the overhead condenser 24 is transported along line 26 to the methanol feed vaporization drum 30 through inlet 32. Optionally the methanol feed stream is transported to line 20 (not illustrated).

The overhead stream comprising primarily methanol enters overhead flash drum 66. Methanol vapors form a methanol vapor stream. The methanol vapor stream is conveyed along line 76 through inlet 78 into the methanol feed vaporization drum. The condensed portion of the overhead stream is withdrawn along line 74 into the top end 42 of the fractionation tower 34.

As noted, the quench bottoms stream comprises methanol and water, which is separated in the fractionation tower 34. A stream of primarily water is withdrawn through outlet 50 in the bottom end 44 and of the fractionation tower 34 is referred to herein as the fractionator bottoms stream. Fractionator bottoms stream passes along line 52, as a wastewater in need of treatment, as a heat source in other locations of the plant, and for other uses such as a quench medium. A reboiler stream from the bottom end 44 is withdrawn along line 56 and is passed through reboiler 58 and returned to the bottom end 44 of the fractionation tower 34.

As noted the methanol feed stream, comprising methanol; is supplied to the methanol feed vaporization drum by lines 20, 26, and 76 through inlets 28, 32, and 78 respectively. The methanol in the feed vaporization drum 30 is separated into a vapor phase and a liquid phase. The vapor phase defining the vaporized methanol feed is withdrawn through outlet 108 along line 110 to inlet 112 of the oxygenate-to-olefins reactor 12. The vaporized methanol feed is converted to an olefin product and leaves the reactor 12 in an effluent stream. The effluent stream is defined as the output stream of the oxygenate-to-olefin reactor. In one embodiment, the effluent stream comprises ethylene, propylene, C4+ olefins, paraffins, water, oxygenates, including dimethyl ether and unreacted methanol feed.

Optionally, controlling the temperature of the reactor is desirable. Temperature control can be accomplished by adding liquid methanol feed to the reactor. In one embodiment, liquid methanol feed is supplied along line 116 to the reactor 12. As the liquid feed vaporizes, heat is removed from the reactor and the temperature is controlled.

According to one embodiment, the weight of ethylene expressed as a percentage of the total weight of the effluent stream as it leaves the reactor is preferably from about 14 wt. % to about 18 wt. %, more preferably from about 15 wt. % to about 17 wt. %, and most preferably about 16 wt. %. According to one embodiment, the weight of propylene expressed as a percentage of the total weight of the effluent stream as it leaves the reactor is preferably from about 14 wt. % to about 18 wt. %, more preferably from about 15 wt. % to about 17 wt. %, and most preferably about 16 wt. %.

According to one embodiment, the weight of water expressed as a percentage of the total weight of the effluent stream as it leaves the reactor is from about 55 wt. % to about 65 wt. %, preferably about 59 wt %. According to one embodiment, the weight of C4+ olefins expressed as a percentage of the total weight of the effluent stream as it leaves the reactor is from about 4 wt. % to about 7 wt. %, preferably 5.6 wt. %. According to one embodiment, the weight of methanol expressed as a percentage of the total weight of the effluent stream as it leaves the reactor is from about 0.5 wt. % to about 1.5 wt. %, preferably about 1 wt. %.

According to one embodiment, the weight of oxygenates other than methanol expressed as a percentage of the total weight of the effluent stream as it leaves the reactor is from about 0.5 wt. % to about 1.5 wt. %, preferably about 1 wt. %.

The effluent stream leaves the reactor at a temperature of from about 800° F. (427° C.) to about 1100° F. (593° C.), preferably from about 900° F. (482° C.) to about 1000° F. (538° C.), more preferably from about 950° F. (510° C.). The pressure of the effluent stream as it leaves the reactor is from about 20 psia (138 kPaa) to about 65 psia (448 kPaa), preferably from about 25 psia (172 kPaa) to about 50 psia (345 kPaa), more preferably from about 25 psia (172 kPaa) to about 40 psia (276 kPaa), most preferably about 37 psia (255 kPaa).

The effluent stream is transported along line 124 to the first heat exchanger 126 and is called the reactor effluent stream in one embodiment. A "heat exchanger" is defined as heat transfer device that transfers heat from one medium to another medium without contacting the one medium with the other medium. The "reactor effluent stream" is defined as an output stream of the oxygenate-to-olefin reactor from the point it leaves the reactor 12 to the first heat exchanger 126. The first heat exchanger 126 heats a stream of high pressure saturated steam with the reactor effluent stream. "High pressure saturated steam" is defined as steam that has a pressure exceeding 400 psia (2758 kPaa) and is saturated with liquid water.

The reactor effluent stream is fed into heat exchanger 126 through inlet 128. High pressure saturated steam is fed into the first heat exchanger 126 through inlet 132. The heat is transferred from the reactor effluent stream to the high pressure saturated steam producing a first cooled effluent stream and a high pressure superheated steam. "High pressure superheated steam" is defined as steam that has a pressure exceeding 400 psia (2758 kPaa) and is not saturated with liquid water. The "first cooled effluent stream" is defined as the output stream of the oxygenate-to-olefin reactor after one step of cooling but before a second step of cooling. Passing the reactor effluent stream through the first heat exchanger 126 is a first step of cooling the effluent stream.

The first cooled effluent stream leaves the first heat exchanger 126 through outlet 130 where the first cooled effluent stream travels, in one embodiment, to a second step of cooling. The high pressure superheated steam leaves the heat exchanger through outlet 134 and travels along line 154.

According to one embodiment, the temperature of the high pressure superheated steam as it leaves the outlet 134 of the first heat exchanger has a temperature ranging from about 500° F. (260° C.) to about 1050° F. (566° C.) and a pressure ranging from about 400 psia (2758 kPaa) to about 1000 psia (6895 kPaa), preferably has a temperature ranging from about 600° F. (316° C.) to about 900° F. (482° C.) and a pressure ranging from about 600 psia (4137 kPaa) to about 950 psia (6550 kPaa), most preferably has a temperature about 700° F. (371° C.) and a pressure of about 625 psia (4309 kPaa).

The first cooled effluent stream is fed along line 136 into a second heat exchanger 138 through inlet 148. Liquid water is fed into the second heat exchanger 138 through inlet 140. The heat is transferred from the first cooled effluent stream to the liquid water producing a second cooled effluent stream and a partially vaporized stream from which the high pressure saturated steam is obtained. The "second cooled effluent stream" is defined as the output stream of the oxygenate-to-olefin reactor after two steps of cooling but before a third step of cooling. Passing the first cooled effluent stream through the second heat exchanger 138 is a second step of cooling the effluent stream. The second cooled effluent stream leaves the second heat exchanger 126 through outlet 146 where the second cooled effluent stream travels, in one embodiment, to a third step of cooling.

According to one embodiment, the temperature of the high pressure saturated steam as it leaves the outlet 140 of the second heat exchanger has a temperature ranging from about 445° F. (229° C.) to about 545° F. (285° C.) and a pressure ranging from about 400 psia (2758 kPaa) to about 1000 psia (6895 kPaa), preferably has a temperature ranging from about 486° F. (252° C.) to about 538° F. (281° C.) and a pressure ranging from about 600 psia (4137 kPaa) to about 950 psia (6550 kPaa), more preferably has a temperature ranging from about 486° F. (252° C.) to about 538° F. (281° C.) and a pressure ranging from about 600 psia (4137 kPaa) to about 700 psia (4826 kPaa), most preferably has a temperature of about 490° F. (254° C.) and a pressure of about 625 psia (4309 kPaa). According to one embodiment, the temperature of the first cooled effluent stream as it enters the second heat exchanger has a temperature ranging from about 555° F. (290° C.) to about 1000° F. (538° C.) and a pressure ranging from about 19 psia (131 kPaa) to about 63 psia (434 kPaa), preferably has a temperature ranging from about 600° F. (316° C.) to about 900° F. (482° C.) and a pressure ranging from about 19 psia (131 kPaa) to about 63 psia (434 kPaa), most preferably has a temperature about 800° F. (427° C.) and a pressure of about 35 psia (241 kPaa).

The high pressure saturated steam leaves the heat exchanger through outlet 142 where it indirectly supplies the first heat exchanger 126 with high pressure saturated steam from line 158. The manner in which high pressure superheated steam is produced from water, according to one embodiment is now disclosed. Liquid water is fed along line 150 into drum 152. The liquid water is maintained in the drum 152 at or near is bubble point. Thus, the steam in the drum 152 is saturated with liquid water. The liquid water is withdrawn along line 156 into the inlet 140 of the second heat exchanger. The second heat exchanger partially vaporizes the water stream. The partially vaporized water stream is from about 5 wt. % to about 80 wt. %, more preferably from about 10 wt. % to about 50 wt. %, and most preferably 15 wt. % to about 40 wt. %.

The steam vapor and liquid water leaves outlet 142 and is transported into drum 152, where a separation of steam vapor from the liquid water occurs. The drum 152 has a liquid space and a vapor space. Typically, enough liquid water is maintained in the liquid space that liquid water is always available for vaporization. The vapor space is typically designed to optimally separate the steam vapor from the liquid water. A portion of the liquid water in the drum 152 is withdrawn and sent to disposal (not shown) to avoid salt and non-volatile build-up in the water circulating from the drum 152 to the second heat exchanger 138.

High pressure saturated steam from the top of the drum 152 is transported along line 158 to the first heat exchanger 126 where the high pressure saturated steam enters inlet 132 and is heated to high pressure superheated steam. The high pressure superheated steam exits the heat exchanger from outlet 134 along line 154. The high pressure superheated steam is used as a heat source in various places in the methanol-to-olefins plant.

The second cooled effluent stream is conveyed along line 160 to a third step of cooling in the third heat exchanger 162 through inlet 164. Liquid water is fed into third heat exchanger 162 through inlet 168. The heat is transferred from the second cooled effluent stream into the liquid water producing a third cooled effluent stream and a partially vaporized stream from which a medium pressure saturated steam is obtained. The "third cooled effluent stream" is defined as the output stream of the oxygenate-to-olefin reactor after three steps of cooling but before a fourth step of cooling. Passing the second cooled effluent stream through the third heat exchanger 162 is a third step of cooling the effluent stream.

According to one embodiment, the medium pressure saturated steam, as it leaves the outlet 166 of the third heat exchanger, has a pressure ranging from about 30 psia (207 kPaa) to about 400 psia (2758 kPaa), preferably has a pressure ranging from about 125 psia (862 kPaa) to about 165 psia (1138 kPaa), most preferably has a pressure of about 145 psia (1000 kPaa). According to one embodiment, the temperature of the second cooled effluent stream as it enters the third heat exchanger has a temperature ranging from about 445° F. (229° C.) to about 800° F. (427° C.) and a pressure ranging from about 18 psia (131 kPaa) to about 61 psia (421 kPaa), preferably has a temperature ranging from about 480° F. (249° C.) to about 700° F. (371° C.) and a pressure ranging from about 18 psia (131 kPaa) to about 61 psia (421 kPaa), most preferably has a temperature about 600° F. (316° C.) and a pressure of about 33 psia (228 kPaa).

The medium pressure saturated steam is produced from water, according to one embodiment that is illustrated as follows. Liquid water is fed along line 172 into drum 176. The liquid water is maintained in the drum 176 at or near its bubble point. Thus, the steam in the drum 176 is saturated with liquid water. The liquid water is withdrawn along line 174 into the inlet 168 of the third heat exchanger 162. The third heat exchanger 162 partially vaporizes the water stream. The partially vaporized water stream is from about 5 wt. % to about 80 wt. %, more preferably from about 10 wt. % to about 50 wt. %, and most preferably 15 wt. % to about 40 wt. %.

The steam vapor and liquid water leaves outlet 170 and is transported into drum 176, where a separation of steam vapor from the liquid water occurs. The drum 176 has a liquid space and a vapor space. Typically enough liquid water is maintained in the liquid space that liquid water is always available for vaporization. The vapor space, typically, is designed to optimally separate the steam vapor from the liquid water. A portion of the liquid water in the drum 176 is withdrawn and sent to disposal (not shown) to avoid salt and non-volatile build up in the water circulating from the drum 176 to the third heat exchanger 162. Steam from the top of the drum 176 exits the drum 176 along line 180.

After this third step of cooling the effluent stream, the third cooled effluent stream, of one embodiment, leaves the outlet 166 of the third heat exchanger and is transported along line 182 to the first methanol boiler system 80. The first methanol boiler system 80, typically, is part of the methanol feed vaporization system 10. According to one embodiment, methanol from the methanol feed vaporization drum 30 is withdrawn along line 84 and enters the fourth heat exchanger 88 through inlet 86. The methanol is vaporized as it passes through the heat exchanger and leaves outlet 90. The methanol returns to the methanol feed vaporization drum 30 as vaporized methanol along line 92. The heat source for this fourth heat exchanger 88 is the third cooled effluent stream.

The third cooled effluent stream is fed along line 182 into the fourth heat exchanger 88 through inlet 184. As noted above, liquid methanol is fed into the fourth heat exchanger 88 through inlet 86. The heat is transferred from the third cooled effluent stream to produce a fourth cooled effluent stream and vaporized methanol. The "fourth cooled effluent stream" is defined as the output stream of the oxygenate-to-olefin reactor after four steps of cooling. Passing the third cooled effluent stream through the fourth heat exchanger 88 is a fourth step of cooling the effluent stream. The fourth cooled effluent stream leave the fourth heat exchanger 88 through outlet 186 where the fourth cooled effluent stream is sent to a quench device along line 188.

According to one embodiment, the methanol, as it leaves the outlet 186 of the fourth heat exchanger 88, has a pressure ranging from about 40 psia (276 kPaa) to about 80 psia (552 kPaa), preferably has a pressure ranging from about 40 psia (276 kPaa) to about 60 psia (414 kPaa), most preferably has a pressure of about 50 psia (345 kPaa). According to one embodiment, the temperature of the third cooled effluent stream as it enters the fourth heat exchanger 88 has a temperature ranging from about 225° F. (107° C.) to about 500° F. (260° C.) and a pressure ranging from about 23 psia (159 kPaa) to about 69 psia (476 kPaa), preferably has a temperature ranging from about 250° F. (121° C.) to about 450° F. (232° C.) and a pressure ranging from about 25 psia (172 kPaa) to about 61 psia (421 kPaa).

As noted, there is a first methanol boiler system 80 in one embodiment. According to at least one embodiment, there is a second methanol boiler system 96. This second methanol fed boiler system 96 functions to add supplemental heat to the first boiler system 80. The liquid methanol is withdrawn from methanol feed vaporization drum 30 along line 100 to methanol boiler 102. The methanol boiler 102 is fed by hot water along line 98. The water is cooled; the methanol is boiled to a methanol vapor. The methanol vapor is returned along line 104 to the methanol feed vaporization drum 30.

The feed vaporization and effluent cooling system, of the present invention, (1) produces high quality steam, (2) boils at least a portion of methanol feed stream and (3) produces a cooled effluent stream that requires less energy to quench in a quench device. All of these objectives are desirable.

Product Quench

As noted, the oxygenate-to-olefin process forms a substantial amount of water as a byproduct. A substantial amount of water can be removed from the cooled effluent stream by a quench device. A "quench device" is a device for removing a portion of the cooled effluent stream by establishing a sufficient quantity of a liquid phase in contact with the cooled effluent stream which condenses at least a portion of the material in the cooled effluent stream. One example of a quench device in an oxygenate-to-olefin product stream is found in U.S. Pat. No. 6,121,504 (direct product quench). The liquid matter that contacts the cooled effluent stream and causes the condensation is called a "quench medium."

In a quench device, at least a portion of the gaseous effluent stream is rapidly condensed through contact with a quench medium in the liquid state (a form of what is typically called "direct contact heat transfer"). When quenching in a quench device, at least a portion of the prime olefins in a gaseous state are separated from the condensed components of the gaseous effluent stream.

According to one embodiment of the present invention, a quench tower is employed as a quench device. In a quench tower, the cooled effluent stream is intimately contacted (i.e., directly exposed in a common volume, and not separated by walls as described above for a heat exchanger) with a quench medium in the liquid state. The quench medium is introduced to the quench tower at a temperature that is both below the quench medium bubble point temperature and the gaseous effluent stream dew point temperature at the lowest pressure within the quench tower. The quench medium is introduced in sufficient volume to cause the cooled effluent stream to move rapidly below its dew point temperature such that a substantial portion of the cooled effluent stream rapidly condenses.

In one embodiment, the temperature of the quench medium is below the quench medium dew point temperature and the aqueous dew point temperature of the cooled effluent stream at the lowest pressure in the quench tower, and causes a substantial portion of the water present in the cooled effluent stream to condense. The quench medium, according to one method of use, is introduced into the quench tower at a location or locations above where the cooled effluent stream is introduced, such that the quench medium will fall within the tower and be contacted with the cooled effluent stream as it, or portions of it including the prime olefins in a gaseous state, rise through the tower. The quench tower typically includes internal elements to facilitate the intimate contacting of the quench medium with the reactor effluent or portions thereof, including liquid distributors and contacting devices such as baffles or trays. Intimate contacting with a liquid quench medium facilitates drawing catalyst fines out of the reactor effluent, into a free-flowing, dilute liquid phase and away from at least a portion of the prime olefins in a gaseous state. The quench tower usually also include other elements, such as heat exchangers used to cool the quench medium that is recirculated into the quench tower.

In a particular embodiment, the quench medium is water. In another embodiment, the quench medium is a portion of the water that has been recovered from the quench tower and cooled (thus reintroduced to the quench tower), and which contains at least a portion of the solids separated from the gaseous effluent stream. In one embodiment, the quench medium is a portion of the water that has been recovered from the bottom of the quench tower.

According to one embodiment, the quench is operated under conditions such that the cooled process gas then enters a quench tower where effluent water is condensed, acetic acid is neutralized and some heavy oxygenates (C3-C4+ aldehydes, ketones & alchols) are rejected. The cooled effluent stream after the quench is defined as the olefin stream.

Product Recovery

After the olefin product stream passes through the quench device, the olefin product stream is further processed to isolate and purify components in the cooled effluent stream, particularly, ethylene and propylene. There are many well-known recovery systems, techniques and sequences that are useful in separating olefin(s) and purifying olefin(s) from the cooled effluent stream. Recovery systems generally comprise one or more or a combination of a various separation, fractionation and/or distillation towers, columns, splitters, or trains, reaction systems and other associated equipment for example various condensers, heat exchangers, refrigeration systems or chill trains, compressors, knock-out drums or pots, pumps, and the like.

Non-limiting examples of equipment used in a recovery system include one or more of a demethanizer, preferably a high temperature demethanizer, a dethanizer, a depropanizer, a wash tower often referred to as a caustic wash tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology, 4th Edition*, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the cooled effluent stream withdrawn from the reactor or converting those products produced as a result of the recovery system utilized.

In one embodiment, the cooled effluent stream withdrawn from the reactor is passed through a recovery system producing one or more hydrocarbon containing stream(s), in particular, a three or more carbon atom ($C_3^+$) hydrocarbon containing stream. In this embodiment, the $C_3^+$ hydrocarbon containing stream is passed through a first fractionation zone producing a crude $C_3$ hydrocarbon and a $C_4^+$ hydrocarbon containing stream, the $C_4^+$ hydrocarbon containing stream is passed through a second fractionation zone producing a crude $C_4$ hydrocarbon and a $C_5^+$ hydrocarbon containing stream. The four or more carbon hydrocarbons include butenes such as butene-1 and butene-2, butadienes, saturated butanes, and isobutanes.

The cooled effluent stream removed from a conversion process, particularly a MTO process, typically has a minor amount of hydrocarbons having 4 or more carbon atoms. The amount of hydrocarbons having 4 or more carbon atoms is typically in an amount less than 30 weight percent, preferably less than 25 weight percent, more preferably less than 20 weight percent, and most preferably less than 15 weight percent, based on the total weight of the cooled effluent stream withdrawn from a MTO process, excluding water. In particular with a conversion process of oxygenates into olefin(s) utilizing a molecular sieve catalyst composition the resulting quenched effluent stream typically comprises a majority of ethylene and/or propylene and a minor amount of four carbon and higher carbon number products and other by-products, excluding water.

Suitable well-known reaction systems as part of the recovery system primarily take lower value products and convert them to higher value products. For example, the $C_4$ hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems include U.S. Pat. No. 5,955,640 (converting a four carbon product into butene-1), U.S. Pat. No. 4,774,375 (isobutane and butene-2 alkylated to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a $C_x$ olefin, wherein x is a number from 2 to 4, in an amount greater than 80 percent, preferably greater than 90 weight percent, more preferably greater than 95 weight percent, and most preferably no less than about 99 weight percent, based on the total weight of the olefin.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent stream fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference.

In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000 that is herein fully incorporated by reference.)

Polymerization processes include solution, gas phase, slurry phase and a high-pressure process, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281,300 describe slurry phase polymerization processes; U.S. Pat. Nos. 4,271,060, 5,001,205, 5,236,998 and 5,589,555 describe solution phase polymerization processes; and U.S. Pat. Nos. 3,917,577, 4,175,169, 4,935,397, and 6,127,497 describe high pressure polymerization processes; all of which are herein fully incorporated by reference.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kPag), preferably in the range of from about 200 psig (1379 kPag) to about 500 psig (3448 kPag), and more preferably in the range of from about 250 psig (1724 kPag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight ($M_w/M_n$) of greater than 1.5 to about 10 as measured by gel permeation chromatography, a melt index ($I_2$) as measured by ASTM-D-1238-E in the range from 0.01 dg/min to 1000 dg/min, a melt index ratio ($I_{21}/I_2$) ($I21$ is measured by ASTM-D-1238-F) of from 10 to less than 25, alternatively a $I_{21}/I_2$ of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, tanks, large hollow articles, rigid food containers and toys, etc.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

The foregoing description of the invention including but not limited to drawing and example are intended to illustrate one or more embodiments of the invention and are non-limiting. While the invention has been illustrated and described herein in terms of the advantages, features, and applications disclosed, a person of ordinary skill in the art will recognize that the invention can be used in other instances or applications. Particularly, other modifications and improvements can be made without departing from the scope and spirit of the invention.

The invention claimed is:

1. A process for producing one or more olefin products from a methanol feed stream in a reactor, the process comprising the steps of:
   (a) supplying the methanol feed stream to the reactor;
   (b) contacting the methanol feed stream with a molecular sieve catalyst composition in the reactor to produce an effluent stream;
   (c) heating high pressure steam with the effluent stream;
   (d) heating medium pressure steam with the effluent stream; and
   (e) recovering the one or more olefin products from the effluent stream, wherein the step of (e) recovering occurs after the step of (d) heating.

2. The process of claim 1, wherein the step of (c) heating comprises the steps of:
   (c-i) heating high pressure saturated steam with the effluent stream to produce high pressure superheated steam; and
   (c-ii) heating water with the effluent stream to produce the high pressure saturated steam, wherein the step of (c-i) heating occurs before the step of (c-ii) heating.

3. The process of claim 1, further comprising the step of:
   (f) heating the methanol feed stream with the effluent stream.

4. The process of claim 3, wherein the step of (c) heating occurs before the step of (d) heating.

5. The process of claim 4, wherein the step of (f) heating occurs after the step of (d) heating.

6. A process for producing one or more olefin products from methanol in a reactor, the process comprising the steps of:
   (a) supplying a methanol feed stream to the reactor;
   (b) contacting the methanol feed stream with a molecular sieve catalyst composition in the reactor and withdrawing an effluent stream having a first temperature;
   (c) cooling the effluent stream in no less than four stages to produce a cooled effluent stream, wherein each of the four stages decreases the effluent stream temperature by no less than 50° F. (28° C.) and wherein the effluent stream has a second temperature after the four stages that is at least 500° F. (280° C.) less than the first temperature.

7. The process of claim 6, wherein the four stages decreases the effluent stream temperature by no less than 75° F. (42° C.).

8. The process of claim 6, wherein the four stages decreases the effluent stream temperature by no less than 100° C. (56° C.).

9. The process of claim 6, wherein the four stages decreases the effluent stream temperature by no less than 125° F. (69° C.).

10. The process of claim 6, wherein the four stages decreases the effluent stream temperature by no less than 150° F. (83° C.).

11. The process of claim 6, wherein the second temperature is at least 600° F. (333° C.).

12. The process of claim 6, wherein the second temperature is at least 700° F. (389° C.).

13. The process of claim 6, wherein the second temperature is at least 800° F. (444° C.).

14. The process of claim 6, wherein the second temperature is at least 900° F. (500° C.).

* * * * *